United States Patent [19]

Pearson et al.

[11] Patent Number: 5,407,814
[45] Date of Patent: Apr. 18, 1995

[54] GENETIC FINGERPRINTING OF YEASTS

[75] Inventors: Bruce M. Pearson, Norwich; Andrew T. Carter, Norwich; Raymond A. McKee, Norwich, all of United Kingdom

[73] Assignee: The Secretary of State for the Minister of Agriculture, Fisheries & Food in Her Britannic Majesty's Government of the United Kingdom of Great Britain and Northern Ireland, London, United Kingdom

[21] Appl. No.: 855,759

[22] Filed: Mar. 20, 1992

[51] Int. Cl.⁶ .................... C12P 19/34; C12Q 1/68; C07H 21/04
[52] U.S. Cl. ........................... 435/91.2; 435/6; 536/24.3; 536/24.32; 536/24.33
[58] Field of Search ............. 435/91.2, 6; 536/24.3, 536/24.32, 24.33

[56] References Cited

U.S. PATENT DOCUMENTS 4,683,202  7/1987  Mullis .................... 435/91.2

OTHER PUBLICATIONS

Nelson et al., *PNAS* 86, 6686–6690 (1989).
Kingsman et al., *J. Mol. Biol.* 145, 619–632 (1981).
Chisholm et al., *Proc. Natl. Acad. Sci USA* 81, 2965–2969 (1984).
Boeke et al., *Mol. Cell. Biol.* 8(4), 1432–1442 (1988).
Hanson et al., Mol. Cell. Biol. 8(12), 5245–5256 (1988).
Lochmuller, et al., "A hot-spot for transposition of various Ty elements on chromosome V in Saccharomyces cerevisiae", Current Genetics, (1989) 16:247–252.

*Primary Examiner*—Margaret Parr
*Assistant Examiner*—Kenneth R. Horlick
*Attorney, Agent, or Firm*—Nixon & Vanderhye

[57] ABSTRACT

The present invention relates to the identification of yeast strains by way of application of the polymerase chain reaction to amplify nucleic acid sequences characteristic of their TY transposon long terminal repeats. Polymerase chain reaction product is analysed, conveniently by agarose gel electrophoresis, and its nature related to the presence of a particular yeast strain or strain type.

11 Claims, 1 Drawing Sheet

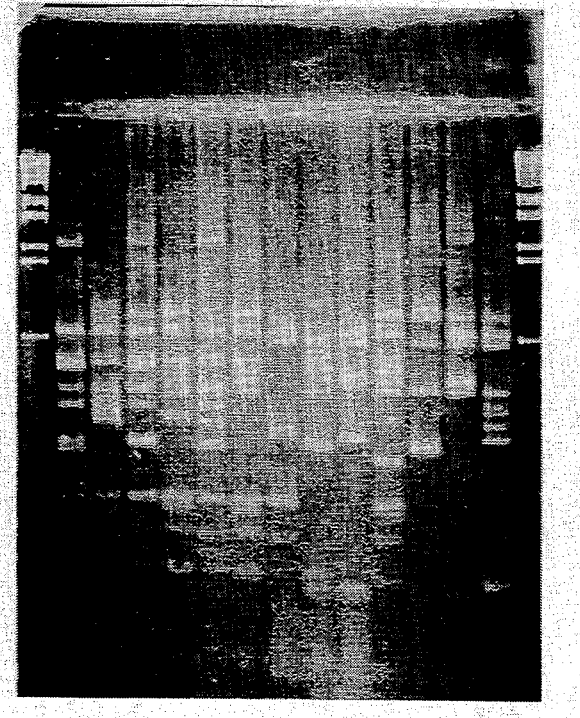

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 35 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:1:

AGCCTTTATC AACAATGGAA TCCCAACAAT TATCT        35

( 2 ) INFORMATION FOR SEQ ID NO:2:

( i ) SEQUENCE CHARACTERISTICS:
        ( A ) LENGTH: 35 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:2:

AGATAATTGT TGGGATTCCA TTGTTGATAA AGGCT        35

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GAATCCCAAC AATTATCT        18

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CCATTGTTGA TAAAGGCT        18

( 2 ) INFORMATION FOR SEQ ID NO:5:

( i ) SEQUENCE CHARACTERISTICS:
        ( A ) LENGTH: 39 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:5:

-continued

ACAGTTTATC AGATTAATTC ACGGAATGTT ACTTATCTT 39

( 2 ) INFORMATION FOR SEQ ID NO:6:

( i ) SEQUENCE CHARACTERISTICS:
      ( A ) LENGTH: 39 base pairs
      ( B ) TYPE: nucleic acid
      ( C ) STRANDEDNESS: both
      ( D ) TOPOLOGY: linear ( i i ) MOLECULE TYPE: DNA (genomic)

( x i ) SEQUENCE DESCRIPTION: SEQ ID NO:6:

AAGATAAGTA ACATTCCGTG AATTAATCTG ATAAACTGT 39

( 2 ) INFORMATION FOR SEQ ID NO:7:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:7:

ACGGAATGTT ACTTATCTT 19

( 2 ) INFORMATION FOR SEQ ID NO:8:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:8:

GAATTAATCT GATAAACTGT 20

GENETIC FINGERPRINTING OF YEASTS

The present invention relates to the identification of yeast strains by way of nucleic acid sequences which vary in their frequency of occurrence and distribution from strain to strain. In particular the present invention provides for the polymerase chain reaction amplification of these characteristic sequences such that production of amplified nucleic acid product will depend upon the particular strain or mixture of strains under investigation.

The genetic fingerprinting of yeasts is a technique which should, inter alia, offer the yeast supply industry, the fermenting industry and others making yeast derived products the ability to monitor their strains for variation and thus improve their quality assurance. Such variations might have deleterious effect upon the quality of products and thus it is vital that a yeast strain can be identified and differentiated from any contaminant yeast strains. Ideally such technique should identify characteristics which vary in a stable manner from strain to strain. A number of approaches have been used to tackle this problem, for example RFLP gene mapping (Panchal et al.,1987), TAFE (Petering et al.,1988) and OFAGE (Takata et al.,1989) which identify differences in chromosomal length.

More recently Walmsley et al. (1989) used probes to the telomere regions of Saccharomyces cerevisiae to differentiate between closely related strains, a method that works outside Saccharomyces species, while Van Vuuren and Van der Meet, (1987) have used protein electrophoresis to give characteristic patterns. These and the above methods are costly in time and materials and limit the number of samples which can be processed.

The present inventors have exploited a different approach based upon characteristic TY regions of the yeast DNA. In 1979 Cameron et al. showed that the transposon TY1 exists in about 35 copies in the haploid genome of Saccharomyces cerevisiae and that its distribution showed some strain to strain variation. It was also shown that the terminal repeats (delta sequences) of the transposon occur independently at a rate of approximately 100 copies per haploid genome. These "solo" deltas were thought to be the result of previous transposition events where the central part of the TY element has been lost through homologous recombination and the delta sequence remains as a "footprint".

The terminal delta sequences from TY1 and TY2 have been found to associate themselves with tRNA gene regions (del Rey et al.,1983; Lochmuller et al.,1989) while other terminal repeat elements such as sigma from TY3 (Clark et al.,1988) and tau from TY4 (Chisholm et al.,1984) are also found in the so called recombination "hotspots". Analysis of the DNA sequences in these areas has now revealed that the delta and sigma elements contain regions of conserved sequence and that the distance between TY elements in Saccharomyces cerevisiae is characteristic of each strain or strain type.

The present inventors have provided a method of determining the identity of a yeast as being of a characteristic strain or strain type by use of the polymerase chain reaction (PCR) to produce products characteristic of the yeast's TY long terminal repeat distribution. Using the PCR to amplify specific regions of DNA in vitro using the thermostable Taq polymerase with specifically designed synthetic oligonucleotide primers targeted at amplifying the parts of the 'hotspot' regions they have found that products characteristic of particular yeast strains or strain types can be obtained.

As the nucleic acid sequences of these repeat elements are found to occur running in both directions within the yeast genome this method allows use of odd numbers of primers directed at their characteristic sequences to derive amplification products; thus even a single primer may potentially give rise to a characterising product which may contain different components to that obtained with multiple primers.

Though the primers can be used in single or pairwise combinations, it has been particularly found that use of the polymerase chain reaction (PCR) in a four primer multiplex system gives a pattern which is particularly adapted for allowing practical comparison between strains, eg. in an industrial test timescale needing 24 hour turnaround. This method avoids the need to isolate and purify DNA from yeast, and produces a rapid fingerprint which can be visualised by agarose gel electrophoresis within a working day.

Multiplex PCR fingerprinting of Saccharomyces cerevisiae offers the opportunity not only of improved characterising capability over existing techniques, but also allows introduction of previously impracticable analytical tests. Many pure research laboratories routinely use a variety of yeast strains, each with different genetic markers and chromosomal complements. Verification of each strain at the beginning of, and throughout, a long term piece of research can be time consuming but essential work. The enablement of the application of PCR in fingerprinting provided by the present invention can not only speed up this process, but also allows rapid authentication of the yeast progeny from mating experiments, and confirmation of the relationship between a diploid yeast and its two haploid parents.

An important consideration for both research scientist and industrialist alike is strain stability. PCR fingerprinting offers due opportunity to monitor natural variation in a strain over a period of years or decades of continuous or discontinuous use.

The test provides sensitivity inter alia because several different sites within the yeast genome are all challenged simultaneously, and the answer to each challenge is an all-or-nothing event. The PCR profile depends upon the juxtaposition of TY long terminal repeat elements which are unlikely to have any bearing upon the biochemical characteristics of the particular yeast strain. This autonomy enables confirmation of integrity of a yeast strain which may have given an otherwise ambiguous biochemical test result.

As well as strain stability the test offers the ability to monitor the relative levels of strains within a mixed culture of Saccharomyces cerevisiae. This is important to brewers who may feel that the particular characteristics of their product rely upon maintenance of perhaps a minority yeast strain population within the starter culture. Once each individual strain has been identified and fingerprinted, any deviation from a diagnostic pattern in terms of proportion or type can be readily detected. This also means that introduction of a wild Saccharomyces cereyisiae yeast into a culture can be detected with equal ease, allowing the brewer to intervene much more swiftly than previously possible. By using the PCR fingerprint of the wild yeast the cause of the contamination can be traced eg. to one of the raw materials. This quality control aspect cannot be over emphasized. Currently, microbiological testing of a fermentation process is often an after-the-event exercise designed only to pinpoint the batch where a particular problem may have arisen. Since, with the present, same day results are standard, on-line surveillance of yeast would be possible even in ale fermentations which last only a few days. This would allow the brewer to determine that no detrimental change had occured to his yeast since inoculation with the starter, and enable him with confidence to use the final biomass for re-pitching.

In its broadest aspect the present invention provides a method for characterising a Feast as being of a particular strain or strain type comprising:

(a) carrying out a polymerase chain reaction using the nucleic acid of the yeast as the reaction template and one or more oligonucleotide primers which are each targeted at nucleic acid sequences characteristic of yeast TY transposon lone terminal repeats and (b) determining the nature of the reaction product from (a) and relating that to the presence of a particular yeast strain or strain type.

The TY transposon long terminal repeats of yeast are typically of some 300 base pairs in length and many such repeat sequences may be found detailed in the literature and commercially available data bases as will be known to the man skilled in the art; eg. from the EMBL data library, Germany. While it is found that targeting of TY transposon long terminal repeats alone will be enough to distinguish between many yeasts the optional targeting of additional primers at other parts of the yeast genome is advantageously used in tandem with these.

A particularly efficacious form of the method of the present invention is provided wherein four or more oligonucleotide primers are used and two are targeted at each of two characteristic sequences selected. Particularly effectively all the primers will be targeted at sequences characteristic of the yeast TY transposon long terminal repeats; more particularly those sequences characteristic of delta, sigma and/or tau element long terminal repeats.

Primers showing good ability to distinguish between various yeasts include those targeted at a sequence characteristic of the TY1 delta element long terminal repeats and primers targeted at a sequence characteristic of TY3 sigma element long terminal repeats and particularly good results are obtained if a four primer multiplex PCR is carried out using a pair of primers for each of these repeats.

The delta and sigma long terminal repeats are of about 300 base pairs in length and characteristic sequences within them may be targeted by a variety of primers with a resultant variation in product for a yeast under investigation. Suitable primers for characterising purposes may be selected by trial and error. Examples of primers targeted at the TY1 delta element long terminal repeats that have been found to be particularly satisfactory in achieving distinctive patterns are those targeted at the double stranded DNA sequence I: (SEQ ID NO:1 or SEQ ID NO:2 )

5'-AGCCTTTATCAACAATGGAATC-
CCAACAATTATCT-3'               SEQUENCE I

3'-TCGGAAATAGTTGTTACCT-
TAGGGTTGTTAATAGA-5'

An example of a suitable primer pair targeted at sequence I are oligonucleotides consisting of sequences II and III (SEQ ID NO:3 and SEQ ID NO:4, Respectively) respectively:

5'-GAATCCCAACAATTATCT-3'      SEQUENCE II

3'-TCGGAAATAGTTGTTACC-5'      SEQUENCE III

Primers targeted at the TY3 sigma element long terminal repeats that have been found to be particularly satisfactory are those targeted at the double stranded DNA sequence IV (SEQ ID NO:5 or SEQ ID NO:6 ):

5'-ACAGTTTATCAGATTAATTCACG-
GAATGTTACTTATCTT-3'           SEQUENCE IV

3'-TGTCAAATAGTCTAATTAAGTGCCT-
TACAATGAATAGAA-5'

An example of a suitable primer pair targeted at sequence IV are oligonucleotides consisting of sequences V and VI (SEQ ID NO:7 and SEQ ID NO:8, respectively) respectively:

5'-ACGGAATGTTACTTATCTT-3'     SEQUENCE V

3'-TGTCAAATAGTCTAATTAAG-5'    SEQUENCE VI

The yeast nucleic acid to be characterised may be included in the PCR reaction mixture in isolated form but is conveniently provided as whole yeast cells. For example cultured yeast sample grown on an agar growth plate or yeast cells grown in liquid culture may be utilised.

In the case of agar cultures a sterile implement may be used to transfer a small part of a colony, eg. about 0.2 mg, to a volume of sterile water, preferably cold, eg. 4° C. or less, in a PCR reaction tube wherein the yeast cells are resuspended and used directly with PCR reaction components.

In the case of liquid cultures a sample volume eg.100 $\mu$l of yeast cells from overnight growth in liquid culture is conveniently transferred to a sterile microcentrifuge tube, centrifuged to provide a pellet (eg. for an eppendorf tube using an eppendorf centrifuge—18,000 rpm for 5 seconds) and the supernatant is removed. A small part of the pellet is resuspended in sterile water as before directly in the PCR reaction tube and used directly with PCR reaction components.

The polymerase chain reaction may thus be carried out by mixing the resuspended sample with all the other reaction components, covering the mixture with a sterile oil (eg. paraffin) overlay and then subjecting the mixture to cycles of temperature suitable for denaturing target duplexes, for annealing of primers to them and for primer extension to produce oligonucleotide fragments in the known way.

The cycles of temperature preferably comprise primer annealing periods at between 45° C. and 62° C. Using the primers II, III, V and VI the optimum primer annealing period temperature for production of readily distinguished product is between 50° C. and 55° C. This temperature will vary, as will be understood by the man skilled in the art, with the length of the primers and the ratio of the bases G, C, T, A therein, and this principle will of course apply whichever transposon long terminal repeat sequence/primer combination is selected.

Feasibilty study;

Four primers II, III, V and VI were designed for their ability to amplify TY element long terminal repeats of selected yeast strains. A wide variety of yeast strains were chosen for evaluation of the PCR fingerprinting technique. All the baking, distilling, lager and wine strains in the UK National Collection of Yeast Cultures were tested. In addition, a selection of the ale and general strains were also examined. The results are presented below.

| Strain type | Number examined | Number of distinct patterns |
|---|---|---|
| A Ale | 100 | 58 |
| B Baking | 12 | 12 |
| D Distilling | 4 | 4 |
| G General | 12 | 11 |
| L Lager | 63 | 26 |
| W Wine | 29 | 26 |
| Total | 220 | 137 |

When Southern blots of restriction-digested chromosomal DNA from different strains were probed with delta sequences from TY1, patterns were found which readily enabled strain differentiation. However, this method requires the isolation, purification, restriction, blotting and Southern analysis of DNA from each yeast strain.

The present invention essentially replaces this time consuming, highly skilled process with one which enables a large sample throughput by relatively unskilled personnel. Moreover, the fragments produced are generally below 2 kb in length allowing the results to be easily interpreted following electrophoresis on a 1.5% agarose gel.

The method of the present invention will now be illustrated by way of exemplification only by reference to the following Figure and protocol example but it will be understood that the number and nature of the primers and conditions shown therein may be varied within its scope.

BRIEF DESCRIPTION OF THE DRAWINGS

FIG. 1: shows the agarose gel electrophoresis patterns given by multiplex PCR of thirteen different NCYC yeast samples using the primers II, III, V and VI as described herein. *=DNA standard.

EXAMPLE

Methods: Taq polymerase was used in 5 units/$\mu$l concentration. 2'-deoxynucleoside 5'-triphosphate solutions (100 mM) were obtained from Pharmacia. Oligonucleotide primers II, III, V and VI were synthesized on an Applied Biosystems 381 A DNA synthesizer using phosphoramidite chemistry and were diluted in 10 mM TrisHCl pH7.6, 1 mM EDTA to 1000 $\mu$g/ml and stored as frozen stocks.

Yeast strains for testing were obtained from the UK National Collection of Yeast Cultures. The yeasts were cultured on YEPD media containing (per liter) 10 g Bacto yeast extract, 20 g Bacto peptone, 20 g glucose, 20 g Oxoid agar. Following growth on plates a sample of colony was removed approx (0.2 mg) and resuspended in 10 $\mu$l ice cold sterile water. 90 $\mu$l of PCR mix was then added and the reaction mix covered with 60 $\mu$l of sterile paraffin oil overlay.

The final reaction mix contains:

10 mM Tris.HCl pH 9.0
50 mM KCl
1.5 mM $MgCl_2$.
0.1% gelatin (w/v)
0.1% Triton X-100
0.2 mM dATP
0.2 mM dCTP
0.2 mM dGTP
0.2 mM dTTP
200 ng of each of the four primers Two units of Taq polymerase were used per reaction. Reactions were carried out in a Hybaid Thermal Reactor on plate control for 30 cycles of 92° C. for 2 minutes, 52° C. for 3 minutes and 72° C. for 2 minutes.

Electrophoresis: Agarose gel was prepared by standard methods (see Maniatis et al: Molecular Cloning, A Laboratory Manual, Second Edition, Pub. Cold Spring Harbour Laboratory Press 1989) using 150 ml TBE electrophoresis buffer (10.8 g Tris Base, 5.5 g boric acid, 4 ml 0.5M EDTA (pH 8.0 ) per liter) to 2.25 g agarose. Approximately 20 $\mu$l aliquots of PCR post reaction mixtures with added loading dye are placed in gel slots made by a 1 mm well comb. Unamplified $\phi$X174 HaeIII or lambda BstEII DNA made up in 788 $\mu$l sterile water, 100 $\mu$l of reaction buffer (100 mM Tris.HCl pH 9.0, 500 mM KCl, 15 mM $MgCl_2$ 1% gelatin, 1% Triton X-100), 8 $\mu$l of a mix of 10 $\mu$l each of the 100 mM 2'-deoxynucleoside-5'-triphosphate solutions, and 2 $\mu$l of 1000 $\mu$g/ml of each primer is placed in a further slot and is run with the reaction samples as a standard.

Electrophoresis was carried out using a constant voltage of 100 volts applied across the gel, positive electrode at the bottom, for a period of about 4 hours until the blue dye has migrated about 10 cm. The gels are developed using ethidium bromide (care, mutagen) at a concentration of 0.5 mg/liter for 30 minutes and viewed under UV light illumination at 302 nm.

The electrophoresis patterns produced proved suitable for the purpose of characterising individual yeast strains or strain types sufficient for ready identification of presence of contaminant yeast to be possible by comparison with standard yeast PCR product patterns. As the products include a variety of oligonucleotide and polynucleotide components derived from sequences found between any two primer hybridization sites it will be seen that performance of two or more PCRs using a different combinations of primers on a given yeast sample each time will provide still further resolving power in investigation of its identity.

It will be realised by the person skilled in the art that the term 'targeted at' as used to describe the primers used in the method of the present invention means that these are capable of hybridizing with the target sequences with a specificity high enough to avoid binding to other parts of the yeast genome to any significant degree. While such specificity may be provided by less than 100% match (G to C and T to A) it is convenient in practice to utilise such 100% match. It will be understood however that the length of a specific primer need not be anything like that of the sequence toward which it is targeted and that suitable primer lengths will thus be of shorter length that their target sequence, conveniently these primers being of the order of 10 to 30 bases long.

In this regard, the present invention further provides kits for performing the method of the present invention, said kits comprising one or more oligonucleotide polymerase chain reaction primers as described in this specification and claimed below.

---

We claim:

1. A method for characterizing a yeast as being of a particular strain or strain type comprising:
   (a) amplifying a nucleic acids in a sample consisting essentially of yeast nucleic acid using a polymerase chain reaction comprising deoxynucleotide triphosphates, polymera a reaction template and at least one, primer, wherein said yeast nucleic acid is said reaction template and said at least one primer comprises one or more oligonucleotide primers which hybridize to regions of nucleic acid of yeast TY transposon long terminal repeats and
   (b) analyzing the reaction product from (a), comparing the analysis with reaction products of particular yeast strains or strain types,
   wherein the nucleic acid to which the primers hybridize is selected from the group consisting of regions represented by SEQ ID NO:1, SEQ ID NO:2, SEQ ID NO: 5 and SEQ ID NO: 6.

2. The method as claimed in claim 1 wherein the primers are selected from the group consisting of primers represented by SEQ ID NO:3, SEQ ID NO: 4, SEQ ID NO: 7, and SEQ ID NO:8.

3. The method as claimed in claim 1 further comprising amplifying with four or more primers such that two of said primers hybridize with each of the TY transposon long terminal repeats.

4. The method as claimed in claim 1 further comprising amplifying with one or more oligonucleotide primers complementary to yeast genome sequences.

5. The method as claimed in claim 1 wherein said sample contains sterile water.

6. The method as claimed in any one of claims 1 to 3 wherein said amplifying further comprises contacting and mixing said sample in polymerase chain reaction components to produce a mixture, covering said mixture with a sterile oil overlay to form a treated sample, and then subjecting treated sample to cycles of temperature suitable for denaturing duplexes, for annealing of primers and for primer extension such that oligonucleotide fragments are produced.

7. The method as claimed in any one of claims 1 to 3 wherein said amplifying further comprises temperature cycles comprising primer annealing periods at from 45° C. to 62° C.

8. The method as claimed in claim 7 wherein the primer annealing period temperature is from 50° C. to 55° C.

9. A kit for the characterization of yeast strains by the method of claim 1 comprising one or more oligonucleotide polymerase chain reaction primers comprising nucleotide sequences which are fully complementary to any one of the nucleic acid sequences of yeast TY transposon long terminal repeats represented by SEQ ID NO:1, SEQ ID NO:2, SEQ ID NO:5 and SEQ ID No:6.

10. The kit as claimed in claim 9 wherein the oligonucleotide primers comprise one pair of primers which hybridize to the double stranded nucleic acid sequence represented by SEQ ID NO:1 or SEQ ID NO:2.

11. The kit as claimed in claim 9 wherein the oligonucleotide primers comprise one pair of primers which hybridize to the double stranded nucleic acid sequence represented by SEQ ID NO:5 and SEQ ID NO:6.

* * * * *